(12) United States Patent
Roberts et al.

(10) Patent No.: US 6,841,689 B2
(45) Date of Patent: Jan. 11, 2005

(54) PROCESS USING CATALYST COMPRISING SOLUBLE POLYMER AND POLYMINO ACID

(75) Inventors: Stanley Roberts, Parkgate (GB); John Skidmore, Herts (GB); Robert Flood, Liverpool (GB); Thomas Geller, Liverpool (GB)

(73) Assignee: Stylacats Limited (GB)

( * ) Notice: Subject to any disclaimer, the term of this patent is extended or adjusted under 35 U.S.C. 154(b) by 0 days.

(21) Appl. No.: 10/296,643

(22) PCT Filed: Jun. 1, 2001

(86) PCT No.: PCT/GB01/02465

§ 371 (c)(1),
(2), (4) Date: Sep. 8, 2003

(87) PCT Pub. No.: WO01/94327

PCT Pub. Date: Dec. 13, 2001

(65) Prior Publication Data

US 2004/0048739 A1 Mar. 11, 2004

(30) Foreign Application Priority Data

Jun. 2, 2000 (GB) .............................. 0013511

(51) Int. Cl.[7] .......................... C07D 301/12
(52) U.S. Cl. ........................ 549/531; 549/90
(58) Field of Search .................. 549/531, 90

(56) References Cited

PUBLICATIONS

Bentley et al. "Towards a Mechanistic Insight into the Juliá–Colonna Asymmetric Epoxidation of a α, β–Unsaturated Ketones Using Discrete Lengths of Poly–leucine", Tetrahedron Letters, NL, Elsevier Schiece Publishers, Amsterdam, vol. 39, No. 50; Dec. 10, 1998, pp. 9297–9300, XP004142700, ISSN: 0040–4039.

Bolm et al. "Asymmetric dihydroxylation with MeO–polyethyleneglycol–bound ligands", Angew Chem. Int. Ed. Engl., vol. 36, No. 7, 1997, pp. 741–743, XP002173252.
Gravert et al. "Organic Synthesis on soluble polymer suports . . . " Chem. Rev., vol. 97, 1997, pp. 489–509, XP002173253.
Flood et al., "Efficient asymmetric epoxidation of . . . ", Org. Lett., vol. 3, No. 5, Mar. 8, 2001, pp. 683–686, XP002173254.
Chemical Abstracts, vol. 132, No. 17, Apr. 24, 2000, Columbus, Ohio, US, Abstract No. 227359, Kim et al., "Possibility of wound dressing using poly(l–leucine). . . . " XP002173255 & Biomaterials 200 (pub. 1999), 21(2), 131–141, Abstract.
Chemical Abstracts, vol. 127, No. 20, Novembner 17, 1997, Columbus, Ohio, US, Abstract No. 283310, Kim et al., "Clonazepam release from . . . " XP002173256 & Arch. Pharm. Res. 1997, 20(4), 324–329, Abstract.
Chemical Abstracts, vol. 100, No. 1, Jan. 2, 1984, Columbus, Ohio, US, Abstract No. 7118, Schmitt et al. "Relationship between conformation . . . " XP0021732157 & Bopolumers 1983 22(8), 1849–1852 Abstract.
Patent Abstracts of Japan, vol. 015, No. 391 (P–1259), Oct. 3, 1991 & JP 03 155527 A (Ajinomoto Co. Inc.), Jul. 3, 1991 Abstract.
Pu, "Recent Developments in Asymmetric catalysis using synthetic polymers with main chain chirality", Tetrahedron: Asymmetry Report No. 36, vol. 9 (1998) 1457–1477.

Primary Examiner—Bernard Dentz
(74) Attorney, Agent, or Firm—Fay, Sharpe, Fagan, Minnich & McKee, LLP

(57) ABSTRACT

There is provided a process for the addition of a nucleophile across an electron poor carbon-carbon double bond (a Michael addition) comprising contacting in a solvent: i) a nucleophile; ii) a compound comprising an electron poor double bond; and iii) a catalyst comprising a soluble polymer and a polyamino acid.

17 Claims, 2 Drawing Sheets

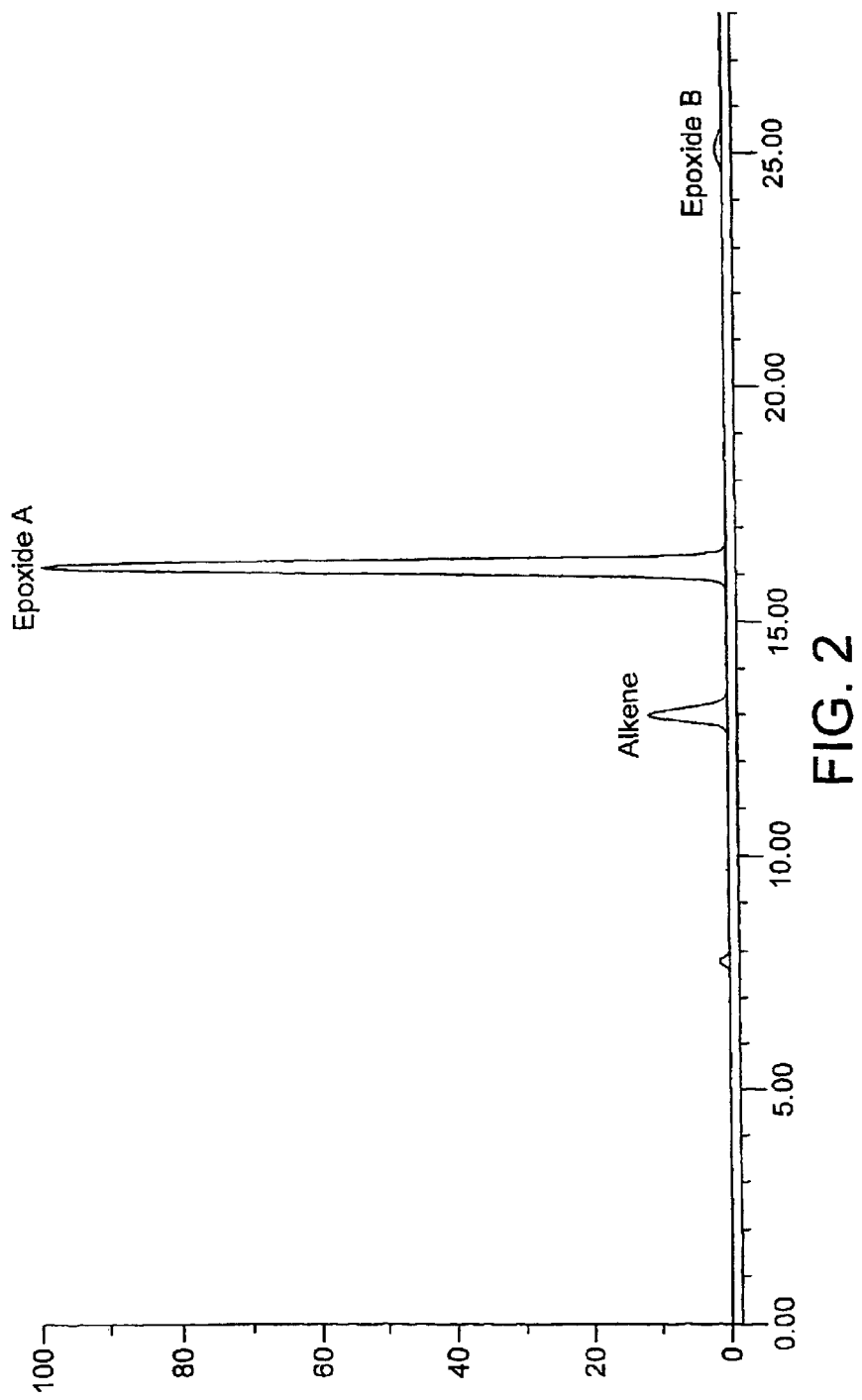

PROCESS USING CATALYST COMPRISING SOLUBLE POLYMER AND POLYMINO ACID

Figure 1:
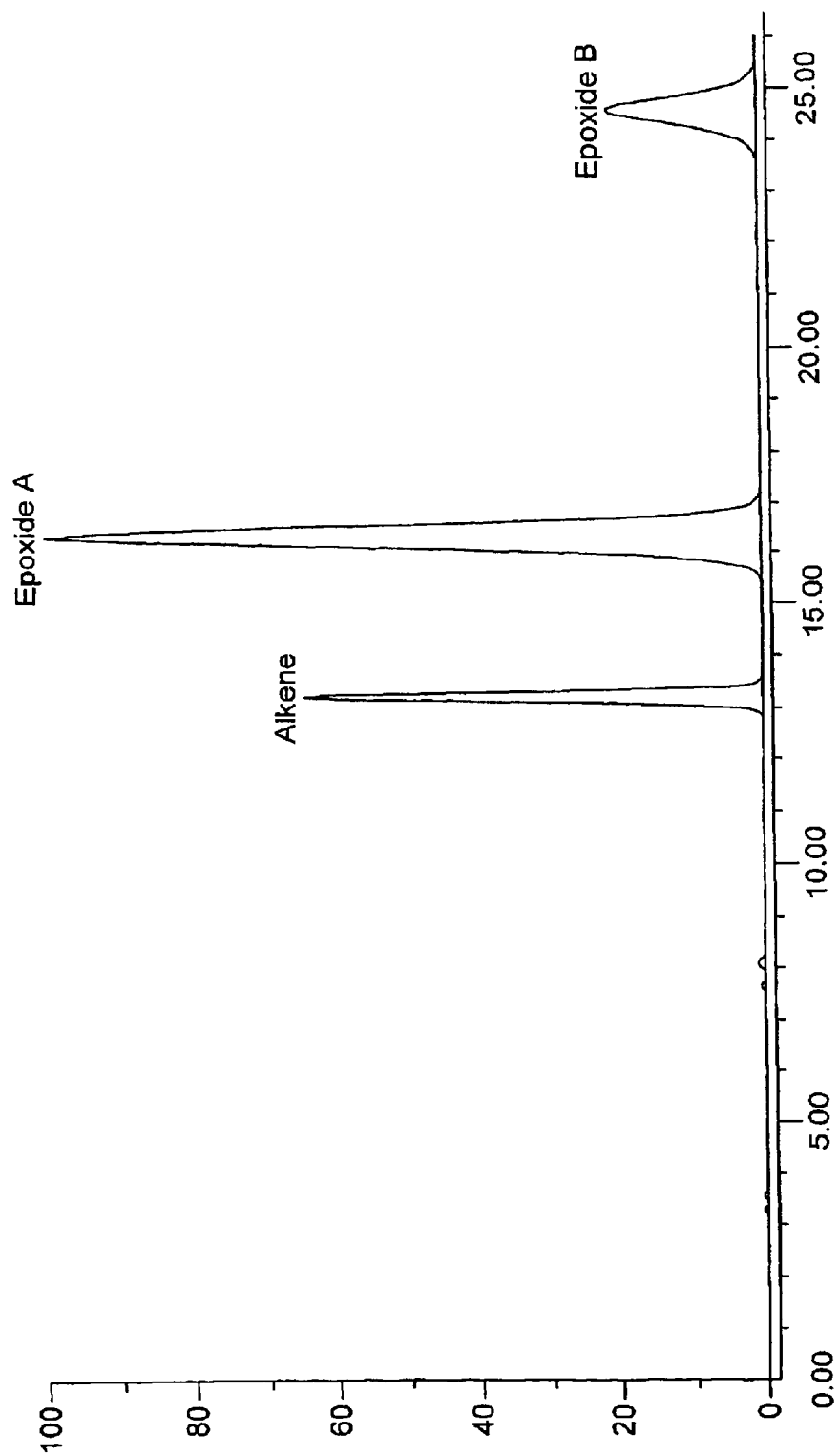

This application is a 371 of PCT/GB01/02465, filed Jun. 1, 2001.

The present invention relates to a catalyst. In particular the present invention relates to a catalyst comprising a polyamino acid which may be utilised in a Michael addition reaction.

The ability of poly-amino adds to catalyse Michael additions such as asymmetric epoxidation[1] was discovered by Juliá and Colonna in 1980[2]. Developments to the chemistry by Roberts[3,4] have broadened the range of substrates, and the methodology has been applied to a range of synthetic targets[5,6].

Prior art system have relied on heterogeneous system wherein the polyamino acid is free or is bound to a solid support.

Tetrahedron Letters, Vol. 39, 1998, 9297–9300 describes an insoluble, *heterogeneous* catalyst involving the attachment of polyamino acids to polystyrene beads via a PEG-spacer.

Tetrahedron: Asymmetry Vol. 9, 1998 by Pu (pp 1457–1477) similarly details asymmetric epoxidations catalysed by insoluble, heterogeneous polyamino acid catalysts.

A review by Gravert and Janda in Chem. Rev. Vol. 97, 1997 (pp 489–509) describes a variety of soluble polymer supports and details (p 495) oligoalanine and oligovaline units linked to glycine-PEG. The linkage of the polyamino acid to PEG Is an ester linkage. The ester linkage would be unsuitable for Michael addition reactions involving basic hydrogen peroxide. Moreover the Review by Gravert and Janda and the initial papers by Bonora et al Gazz Chim Ital., 1980, 503 and Makromol Chem., 1979, 2095 do not teach the reader how to accomplish Michael addition reactions such as asymmetric epoxidation reactions. No mention is made of any catalytic function of the PEG-o-Gly-polyamino acids.

The prior art systems which have relied on heterogeneous system exhibit a number of disadvantages. These systems provide low enantiomeric excess, particularly in systems comprising short chain (<10) amino acids Furthermore, the heterogeneous nature of such system may limit their industrial applicability for reasons of ease of handling, slow reaction rates and limited substrates. Moreover heterogeneous systems are not readily characterised by IR and NMR techniques.

The present invention alleviates the problems of the prior art.

In one aspect the present invention provides a process for the addition of a nucleophile across an electron poor carbon-carbon double bond (a Michael addition) comprising contacting in a solvent (i) a nucleophile; (ii) a compound comprising an electron poor double bond; and (iii) a catalyst comprising a soluble polymer (SSL) and a polyamino acid (PAA).

It will be appreciated by one skilled in the art that by the term "Michael addition" it is meant an addition of a nucleophile across a double bond conjugated with an electron withdrawing group. The epoxidation of an enone, a typical Michael addition, is exemplified below:

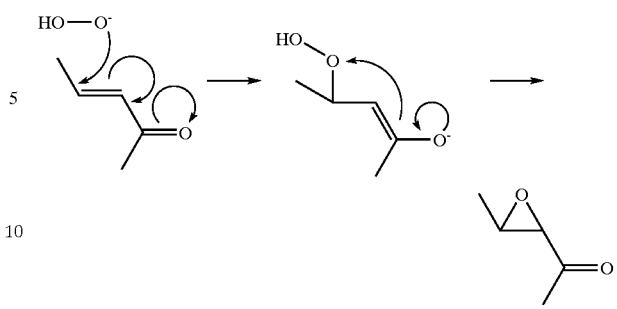

In the present specification by the term "electron poor" it is meant a group having an electron withdrawing group on at least one terminal atom of the double bond.

In the present specification by the term "polyamino acid" it is meant a compound comprising two or more linked amino acid units. Such compounds comprising a relatively low number of amino acid units may sometimes be referred to as oligoamino acids.

The following abbreviations are used in the present specification

Amino-PEG: polyoxyethylene (bis) amine [purchased from Sigma, made from PG of MW 3350]
AR: analytical reagent
Boc: tert-butoxycarbonyl
DBU: 1,8-diazabicyclo[5.4.0]undec-7-ene
DOM: dichloromethane [was distilled from calcium hydride]
DIC: 1,3-diisopropylcarbodiimide
DMF: dimethylformamide [was purchased dry from Avocado and stored under $N_2$]
ee: enantiomeric excess
Fmoc: 9-fluorenylmethoxycarbonyl
HBTU: 2-(1H-benzotriazole-1-yl)-1,1,3,3-tetramethyluronium hexaflurophosphate
HPLC: high performance liquid chromatography
Leu-NCA: L-leucine N-carboxyanhydride
M-PEG: polyethylene glycol monomethyly ether [various MW products purchased from Fluka]
PEG: polyethylene glycol [polyoxyethylene]
PLL: poly-l-leucine
UHP: Urea-hydrogen peroxide complex It has been found that the catalysts of the present invention offer a number of advantages. For embodiments of the present invention these advantages include:

for a given chain length of PAA, Increased catalytic activity may be observed. Less catalyst is therefore required for a given activity and the catalyst cost is reduced the provision of a solubilised catalyst allows for catalysis in a homogeneous system. Homogeneous systems provide
increased reaction speeds
increase in the number of possible substrates
increased degree of selectivity With regard to the high degree of selectivity it has been identified that an enantiomeric excess far in excess of that of the prior art may be achieved by the process of the present invention. The enantiomeric excess is calculated using the following formula $$ee = \frac{(A-B)}{(A+B)} \times 100$$

wherein A is the amount of desired enantiomer and B is the amount of undesired enantiomer.

The homogeneous of the present invention allows for the operation of the process in a continuous manner. The homogeneous catalyst system may be introduced into a membrane reactor comprising a semi-permeable membrane wherein the membrane is impermeable to the substrate and catalyst and permeable to the reaction product. The catalyst is retained in the reactor. Substrate may be fed to the reactor and on conversion it may pass across the membrane and out the reactor. Such continuous operation is not possible with the heterogeneous systems of the prior art because the heterogeneous catalyst will block the membrane.

Nucleophile

Preferably the nucleophile of the present process is selected from oxygen and sulphur. More preferably the nucleophile is oxygen.

When the nucleophile is oxygen, the oxygen nucleophile is preferably provided by a peroxide group.

When the nucleophile is sulphur, the sulphur nucleophile may be provided by a $^-$SPh group.

Compound Having Electron Poor Double Bond

Preferably the double bond is a carbon-carbon double bond.

As disclosed above an electron withdrawing group is attached to a terminal atom of the double bond of (ii). The electron withdrawing group may be selected from carbonyl, —CN and —NO$_2$.

In a preferred aspect the double bond is a carbon-carbon double bond and the electron withdrawing group is a carbonyl group. In a particularly preferred aspect the electron withdrawing group and the carbon-carbon double bond comprise an enone group. In a highly preferred aspect the compound comprising the electron poor double bond is a compound of the structure

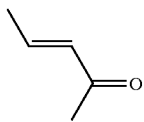

Catalyst

In preferred aspects of the present invention the catalyst is of the formula or comprises a group of the formula SSL-linker-PAA, wherein "linker" is a linker bond or an optional linker group.

Further preferred catalysts include those of the formula X-SSL-linker-PAA-Y, or X-PAA-linker-SSL-linker-PAA-Y, wherein X and Y are independently selected from OMe and NH$_2$, and "linker" is a linker bond or an optional linker group.

In each of the aspects above preferably Y is NH$_2$.

Linker

It is preferred that the linker is non-cleavable under the reaction conditions of the present process. It has been identified that a preferred non-cleavable linker bond is an amide bond.

The SSL-linker-PAA catalyst is typically prepared from SSL-(linking group) and PAA. In this aspect the linking group is or comprises a nucleophilic group. The nucleophilic linking group with attack the PAA to provide the corresponding linker group. Preferably the linking group is or comprises a —NH$_2$ group. More preferably the linking group is selected from —O-hydrocarbyl-NH$_2$, -hydrocarbyl-NH$_2$, —C(CH$_2$NH$_2$)$_2$(NH$_2$).

For linking groups such as —C(CH$_2$NH$_2$)$_2$(NH$_2$).more than one linking moiety is provided for attachment to a PAA. In these aspects the catalyst may be of the formula or comprise a group of the formula SSL-linker-(PAA)n, wherein n is an integer greater than 1.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably the hydrocarbon of the linking group is C$_{1-6}$ alkyl, more preferably (CH$_2$)$_{1-6}$.

The PAA may be attached to the linking group by formation of the PAA and subsequent connection to the linking group, or may be synthesised by stepwise addition of amino acid units to the linking group.

PAA

The polyamino acid may be a homopolymer of one amino acid selected from, or a copolymer consisting of two or more amino acids selected from, cysteine, glycine, neopentyiglycine, alanine, valine, leucine, norleucine, phenylalanine, tyrosine, serine, cystine, threonine, methionine, di-iodotyrosine, thyroxine, dibromotyrosine, tryptophan, proline, hydroxyproline, aspartic acid, glutamic acid, β-hydroxyglutamic acid, omithine, arginine, lysine and histidine.

Preferably the polyamino acid is a homopolymer of one amino acid selected from, or a copolymer consisting of two or more amino acids selected from, leucine, alanine and neopentylglycine. In a highly preferred aspect the polyamino acid is a homopolymer of leucine.

Thus in a further aspect the present invention provides a catalyst comprising a soluble polymer and a polyamino acid, wherein the polyamino acid is a homopolymer of an amino acid selected from, or a copolymer consisting of two or more amino acids selected from, leucine, alanine and neopentylglycine.

The PAA preferably contains from 2 to 50, preferably 5 to 25, more preferably 5 to 15, for example 5, 10 or 15 amino acid residues.

SSL

The soluble polymer is selected such that the catalyst is soluble in the solvent in which the present process is conducted. The soluble polymer may be a homopolymer or a copolymer of monomers selected from styrene, vinyl alcohol, ethylene imine, acrylic acid, methylene oxide, ethylene glycol, propylene oxide and acrylamide.

In a preferred aspect the soluble polymer is polyethylene glycol (PEG) or a derivative thereof. Derivatives include polyethylene glycol monomethyl ether (M-PEG) and polyethylene glycol(bis)amine [amino-PEG].

The SSL or the solvent system of the present process may be selected such that the catalyst may be easily recovered after use in the present process. A SSL may be chosen which is soluble in one solvent and yet insoluble in a second solvent. After reaction the catalyst may be extracted into the second solvent. The insolubility of the SSL in this solvent will result in release of the catalyst from solution. The catalyst may then be readily collected, for example by filtration.

EXAMPLES

In the present Examples soluble catalysts are constructed by initiating the polymerisation of L-leucine N-carboxyanhydride with amino-PEG of average MW 3500 (above). This amine is preferred to underivatized PEG as an amide linkage to the growing polypeptide is desirable in order for the catalyst to be stable under the basic conditions utilised for epoxidation. It has been shown that the average chain length required for a good asymmetric catalyst has been reduced by the use of soluble catalysts. Using soluble catalysts with an average chain length as low as 5, the test substrate chalcone may be epoxidized (below) with an ee of 97%; far greater than for using an oligoleucine 5 mer supported on an insoluble resin. Exact numbers of leucine residues have been coupled to the support using solution phase peptide synthesis to investigate this further.

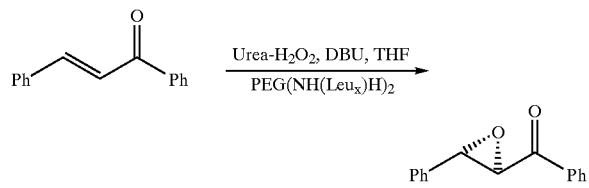

10 mer L-leucine N-carboxyanhydride with amino-PEG was used in the above catalysis and compared to the catalysis provided by an analogous 10 mer heterogeneous amino acid of the prior art. The HPLC traces of the reaction products are shown as FIGS. 1 and 2. The highlighted peaks are

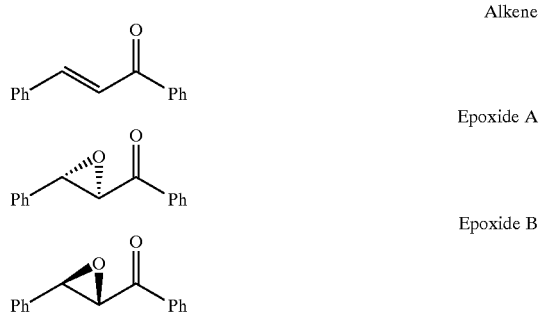

Alkene

Epoxide A

Epoxide B

It can be clearly seen from these traces that the catalyst of the present invention provides both a high degree of conversion and a high ee when compared to the heterogeneous system of the prior art.

Example 1

Synthesis of Polyleucine on Polyethylene Glycol Monomethyl Ether (M-PEG)

Although some respectable ee s were observed for catalysts of this type, two main problems hampered this approach. Firstly, the difficulty of obtaining a dry enough sample of M-PEG to ensure that this, rather than any water present, initiated the polymerisation of the leu-NCA Also, during the epoxidations the catalysts gradually appeared to precipitate out of solution, most likely due to cleavage of the ester bond between the polypeptide and the solubilising support.

To avoid these difficulties, amino-PEG [$H_2N(CH_2CH_2O)_xCH_2CH_2NH_2$] was instead used as the initiator. As amines are generally more nucleophilic than alcohols or water, trace water present in the sample cannot compete effectively as an initiator for the leu-NCA; furthermore the resulting amide linkage to the polypeptide is stable under the basic epoxidation conditions and the catalysts do not therefore precipitate from the reaction solution.

Example 2

Synthesis and Testing of Polyleucine on Amino-PEG (1st Batch)

Leu-NCA (164.5 mg, 1.048 mmol) and amino-PEG (140 mg, 0.4179 mmol, 1/25 eq) were dried overnight at a temperature of 90° C.(the amino-PEG had also been previously dried at 1.1 mbar for 5.5 hr) and stirred together in dry THF (1 5 ml) under nitrogen.

IR after 3 days showed much PLL (1654 $cm^{-1}$) and little NCA. After 7 days diethyl ether (250 ml) was added to precipitate the product, which was washed in a sinter with more diethyl ether (3×100 ml) and dried to yield 268 mg (a quantitative yield) of the white solid [$H(L-Leu)_xNH$]$_2$PEG (X=12.5 by assumption).

Testing of the 1st Batch Amino-PEG-PLL for Homogeneous Epoxidation in (a) THF and (b) $CCl_4$ 60.3 mg of the product was placed in separate vials and stirred in (a) THF and (b) $CCl_4$ respectively for 1 hour. The solution (a) and suspension (b) were then filtered through paper to two separate vials (a) and (b) respectively, to which a further 1 ml of the solvent was added.

To (a) was added chalcone (50 mg), UHP (35 mg, 1.5eq) and DBU (75 µL, 2 eq).

To (b) was added 4M NaOH (2 ml), chalcone (50 mg) and 30% aq $H_2O_2$ (0.25 ml). A further 0.25 ml was added to (b) after 8 hrs.

| Time/h | % C (a) | % ee (a) | % C (b) | % ee (b) |
|---|---|---|---|---|
| 0.5 | 31 | 43 | — | — |
| 1 | 50 | 34 | — | — |
| 2 | 72 | 31 | — | — |
| 3 | 81 | 31 | 13 | 5 |
| 8 | 96 | 32 | 19 | 13 |
| 20 | 98 | 29 | 35 | 55 |
| 50 | — | — | 53 | 59 |

Testing of the 1st Batch Amino-PEG-PLL for Homogeneous Epoxidation in (c) DME/$H_2O$, and (d) Toluene/NaOH To (c) 59.6 mg and (d) 59.5 mg of the polyleucine was added DME/$H_2O$ 1:1 (2 ml) and toluene/NaOH 1:1 (2 ml) respectively. After 4 hr stirring, (c) and (d) were filtered through paper to vials, using a further 2 ml of the same solvent mixtures.

To (c) was added chalcone (50 mg) and Na₂CO₃.1.5H₂O₂ (56 mg, 1.5 eq).

To (d) was added chalcone (50 mg) and H₂O₂ (30% aq, 0.5 ml).

| Time | % C (c) | % ee (c) | % C (d) | % ee (d) |
|------|---------|----------|---------|----------|
| 1 h  | 21      | 0        | 0       | —        |
| 21 h | 51      | 0        | 19      | 1        |
| 7 d  | 54      | 0        | 21      | 0        |

Conditions (e), H₂O₂ aq, DBU and THF gave a rapid reaction but no ee.

Example 3

Synthesis and Testing of Polyleucine on Amino-PEG (2nd Batch)

Preparation: Leu-NCA (1.198 g, 20 eq) and amino-PEG (0.6384 g) were stirred in THF (30 ml) for 5 days. IR showed no NCA remained, so the product was precipitated with diethyl ether (500 ml), washed with more ether in a sinter and dried, yielding 1.3557 g (90%) of the product.

Testing: 100 mg of this partially soluble (37% in THF) catalyst was stirred with UHP (100 mg) in THF (1.8 ml) and DBU (0.2 ml) for 20 min, then filtered to a vial containing chalcone (50 mg) in THF (2 ml). Progress was monitored by HPLC (see over).

| Time/h | % C | % ee |
|--------|-----|------|
| 1      | 56  | 80   |
| 2      | 62  | 77   |
| 3      | 63  | 75   |
| 5*     | 66  | 73   |
| 24     | 99  | 55   |

*a further oxidising solution (100 mg UHP/2 ml THF/20 min stir) was filtered in using another 1 ml THF.

A sample of this catalyst was sent for microanalysis.

Only 6 mg of the catalyst was recovered from a sinter after precipitation with ether, this gave an ee of 2–5% when tested exactly as above with 50 mg chalcone, due to the background reaction. It is believed that testing with the substrate and oxidant used on a smaller scale would have seen a higher ee.

Further Work with the 2nd Batch Amino-PEG-PLL

Subsequently it was shown that higher ees could be obtained with this batch of catalyst, and an improved recovery procedure utilising membrane filters increased the ee with recycled material.

The 2nd batch amino-PEG-PLL (1.05 g) was stirred in THF (100 ml) and filtered after 80 min. From the sinter was recovered 345 mg insoluble catalyst. It seems likely that this product is due to trace moisture getting in the NCA during storage and causing some to polymerise prior to the addition of the amino-PEG initiator. Soluble catalyst 391 mg (37%) was recovered from the filtrate. 104 mg of the soluble and insoluble fractions were placed in separate vials with THF (4 ml) and chalcone (50 mg). Oxidising solution X (1.4 mL) was then added, and the reactions monitored by HPLC. Oxidising solution Y (1.4 ml) was added after 3 h to both reactions:

| Time | % C (insol) | % ee (insol) | % C (sol) | % ee (sol) |
|------|-------------|--------------|-----------|------------|
| 1 h  | 33          | 93           | 45        | 92         |
| 2 h  | 45          | 91           | 58        | 95         |
| 3 h  | 56          | 91           | 66        | 94         |
| 5 h  | 63          | 89           | 77        | 93         |
| 8 d  | 99          | 87           | 99        | 93         |

X: UHP (200 mg), DBU (0.4 ml), THF (3.6 ml) stirred for 20 min then filtered.

Y: As X except the DBU is replaced by THF (0.4 ml).

Recovery Procedure

The soluble fraction was precipitated with diethyl ether and recovered using HPLC membrane filters, which were separately washed carefully with diethyl ether and water, collected and washed with THF to recover the catalyst, along with some by-products e.g. epoxychalcone. The THF solution was dried (MgSO₄), filtered and the solvent removed in vacuo to give 213 mg of solid material containing catalyst (48% max). 1 00 mg of this product was tested in exactly the same conditions as before, except for the timing of the addition of the second oxidising solution:

| Time | % C | % ee |
|------|-----|------|
| 1    | 27  | 62   |
| 4    | 48  | 49   |
| 5*   | 58  | 44   |
| 23   | 96  | 32   |

*oxidising solution Y added.

Example 4

Synthesis and Testing of Polyleucine of Average Chain Lengths 5–25 on Amino-PEG Preparation of the L-Leucine NCA L-Leucine (15.00 g, 0.1144 mol) was heated to 100° C. under vacuum overnight, suspended in THF (150 ml) and stirred at 45° C. in a 3-neck flask with a reflux condenser fitted, under N₂ pressure. Triphosgene (13.574 g, 0.4 eq) was added via a solid addition tube. After ca 80 min, the reaction had gone clear and the mixture was washed with dry diethyl ether (1 L) through the filter agent Celite (5 cm deep) in a sinter funnel (diameter 8 cm porosity 3) to a RB flask.

The solvents were removed in vacuo and the residue redissolved in the smallest possible volume (ca 80 cm³) of THF. Hexane (1 L) was added to precipitate out the NCA; the flask was placed in an ice bath for 30 min. The precipitate was filtered off and dried to obtain 8.88 g (49%) of L-Leu-NCA as a white crystalline solid.

Polymerisation of the Leu-NCA

Five reactions were set up, with the intended products being [H(L-Leu)$_x$NH]₂PEG with X=5, 10, 15, 20, 25. The Soxhlet extractor washed amino-PEG was used as the initiator.

5 mer: Initiator 0.5146 g; L-Leu NCA 0.3667 g(10 eq); THF 50 ml 10 mer: Initiator 0.5146 g; L-Leu NCA 0.7333 g(20 eq); THF 50 ml 15 mer: Initiator 0.5146 g; L-Leu NCA 1.100 g(30 eq); THF 50 ml 20 mer: Initiator 0.5146 g; L-Leu NCA 1.4667 g(40 eq); THF 100 ml 25 mer: Initiator 0.5146 g; L-Leu NCA 1.8333 g(50 eq); THF 100 ml Calculations of equivalents based on microanalysis result; N content of washed amino-PEG=1.27% (all N assumed to be available as initiator) and the NCA MW (157.1679). All reactions had a few activated 4 Å molecular sieves added to the flask and were stirred at RT under $N_2$.

Workup: After 8 days each reaction was added to ether (500 ml) and washed into a sinter funnel. The sieves were extracted with tweezers, washing with diethyl ether. Ether (2×200 ml) was used to wash the product, then a new flask was placed under the sinter funnel and the soluble product collected by washing with THF (2×100 ml) followed by removing the filtrate in vacuo. The mass of the insoluble polyleucine remaining in the sinter was also recorded in each case.

| Reaction | Yield of soluble polyleucine | Yield of insoluble polyleucine |
|---|---|---|
| 5mer | 0.53 g | 0.210 g |
| 10mer | 0.37 g | 0.756 g |
| 15mer | 0.49 g | 1.137 g |
| 20mer | 0.45 g | 0.942 g |
| 25mer | 0.62 g | 1.748 g |

Microanalysis on these Samples

The soluble samples were submitted for microanalysis, and there are two ways to analyse the data obtained:

(i) If we assume the amino-PEG is fully bifunctionalised, the N content of 1.27% puts the MW at 2205.

(ii) From the MALDI data (section 13) the average MW is approximately 3470. The nitrogen content of 1.27% means that the MW of nitrogen in one polymer of PEG is on average 44.069, putting the average degree of functionalization at 3.1462.

Whether method (i) or (ii) is used, we first have to use the microanalysis data to calculate the proportion of PLL in each sample. We know that the percentage of N in the leucine repeat unit is 12.37% and in amino-PEG it is 1.27%, so where the sample N content falls (between these two values) will give the percentage of polyleucine in our sample. The microanalysis results for our catalysts are as follows:

| Chain length | % N found | % C found | % H found | % PLL in sample |
|---|---|---|---|---|
| 5 | 4.54, 4.53 | 56.29, 56.30 | 9.25, 9.27 | 28.6 |
| 10 | 6.09, 6.10 | 58.18, 58.24 | 9.49, 9.47 | 43.4 |
| 15 | 7.44, 7.45 | 58.47, 58.60 | 9.44, 9.46 | 55.5 |
| 20 | 7.33, 7.28 | 58.34, 58.18 | 9.45, 9.42 | 54.3 |
| 25 | 8.04, 8.02 | 59.24, 59.15 | 9.44, 9.43 | 60.9 |

Example of Calculation:

% N (PLL)×Proportion PLL (Y)+% N (PEG)×Proportion (PEG)=% N (SAMPLE)×1

12.378% Y+(1−Y)×1.27%=% N (SAMPLE)

$$Y = \frac{\% N (SAMPLE) - 1.27\%}{11.108\%}$$

So for the 5 mer, % N (SAMPLE)=4.535 (av)

$$\text{So } Y, \text{ proportion (PLL)} = \frac{4.535\% - 1.27\%}{11.108\%} = 0.286 = 28.6\%$$

Calculation of the Chain Length, Using Method (ii)

$$\text{For 5mer, } \frac{MW(PLL)}{MW(PEG) + MW(PLL)} = 0.286$$

So MW(PLL)=0.286MW(PEG)+0.286MW(PLL)

0.714MW(PLL)=0.286MW(PEG)

$$\frac{1389.94}{3.1462} = 441.79 \quad (\text{MW per chain})$$

$$\frac{441.79}{113.1589 \text{ (leu repeat unit)}} = 3.904$$

| Intended average chain length | Average chain length according to data |
|---|---|
| 5 | 3.904 |
| 10 | 7.473 |
| 15 | 12.156 |
| 20 | 11.595 |
| 25 | 15.154 |

Testing of this Series of Catalysts for Epoxidation 5 vials were loaded with amino-PEG-PLL and chalcone as below:

| Intended chain length | Catalyst/mg | PLL mass/mg | chalcone used/mg |
|---|---|---|---|
| 5 | 57.3 | 16.84 | 16.84 |
| 10 | 33.6 | 14.59 | 14.59 |
| 15 | 77.0 | 42.80 | 42.80 |
| 20 | 16.2 | 8.80 | 8.80 |
| 25 | 96.0 | 58.42 | 58.42 |

UHP (0.5 g) was dissolved in THF (49.5 ml) and DBU (0.5 ml), pre stirred under $N_2$ pressure for 20 min then filtered. 0.1 ml/mg chalcone was added to each reaction after 0 and 4 hr. After 4 days, UHP (570 mg) was stirred in THF (25 ml), stirred under $N_2$ for 20 mins and filtered. 0.1 ml/mg chalcone of this solution was also added to each reaction.

| Chain length Time | 5mer % C/% ee | 10mer % C/% ee | 15mer % C/% ee | 20mer % C/% ee | 25mer % C/% ee |
|---|---|---|---|---|---|
| 1 h | 39/96.9 | 39/97.1 | 34/97.2 | 36/97.7 | 26/97.2 |
| 2 h | 38/97.4 | 39/96.4 | 33/97.4 | 37/97.6 | 27/96.4 |
| 4 h* | 37/97.2 | 39/97.8 | 33/97.6 | 35/— | 28/96.6 |
| 24 h | 80/97.5 | 80/96.6 | 58/96.4 | 63/95.0 | 39/92.8 |
| 4 d* | 81/97.4 | 77/95.8 | 59/96.4 | 68/92.6 | 42/91.1 |
| 10 d | 98/96.0 | 100/96.1 | 88/87.8 | 94/85.4 | 66/77.9 |

*extra oxidant added (see above).

Titrations on Solubility of UHP in THF
Equation:

$5H_2O_2 + 2KMnO_4 + 3H_2SO_4 = MnSO_4 + K_2SO_4 + 8H_2O + 5O_2$ MW 34.012 MW 158.04 98% aq.

UHP=$H_2NCONH_2 \cdot H_2O_2$, MW 94.07

Solution 1: UHP (0.500 g) was dissolved in THF (49.5 ml) and DBU (0.5 ml), stirred for 20 min at RT and filtered. 36.35 cm$^3$ of this solution decolourised 33.4 mg KMnO$_4$ in H$_2$O/H$_2$SO$_4$, so conc. of H$_2$O$_2$ present=0.0145 mol.dm$^{-3}$, 100% dissolution of the H$_2$O$_2$ from the UHP would be 0.1063 mol.dm$^{-3}$, so % dissolution=13.67%.

Solution 2: As above, except 0.550 g UHP used and the mixture stirred for 40 min. 30.85 cm3 of this solution neutralised 53.1 mg of acidified aqueous KMnO$_4$, so conc. of H$_2$O$_2$ present=0.0218 mol.dm$^{-3}$. 100% dissolution here would have been a conc. of 0.1169 mol.dm$^{-3}$, so 18.66% of the H$_2$O$_2$ dissolved this time.

Example 5

Synthesis and Testing of Polyleucine of Average Chain Length 3 on Amino-PEG (2 Batches)

First 3 mer- Preparation: Leu-NCA (0.2143, 3 eq) and the Soxhlet extractor washed amino-PEG (0.5014 g) were stirred in THF (50 ml) under N$_2$ pressure at RT. IR after 2 days showed no NCA present, so diethyl ether (200 ml) was added to precipitate the product, which was washed in a sinter with more ether (2×100 ml). THF (4×50 ml) was used to extract the soluble polymer product, the THF being removed in vacuo to yield [H(L-Leu)$_3$NH]$_2$PEG (566.5 mg). Microanalysis: C=54.55, 54.59: H=9.30, 9.32: N=2.97, 2.99: Av. chain length=1.77.

Second 3 mer- Preparation: Exactly the same as above, even the same NCA was used. This had been stored in a dessicator for the weeks between these preparations. For the testing of these Catalysts see Example below "Further Test Results With 5–25 mers".

Example 6

Synthesis, in Methanol of Polyleucine of Average Chain Length 5 on Amino-PEG

Leu-NCA (69.1 mg, 5 eq) and amino-PEG (97.0 mg, dried but not wad in a Soxhlet extractor) were stirred under N$_2$ in AR methanol containing anhydrous MgSO$_4$ (1.17 g). IR after 2 days showed no NCA, so the methanol was removed, the solid product washed in a sinter funnel several times with diethyl ether, and the soluble product extracted with THF (28.6 mg). For test results see Example below "Adsorbtion of a Soluble Catalyst onto Silica".

Example 7

Synthesis of Exact Chain Length (1,2,3,4) Polyleucine on Amino-PEG

The scheme below outlines a synthesis of soluble polymer supported peptides:

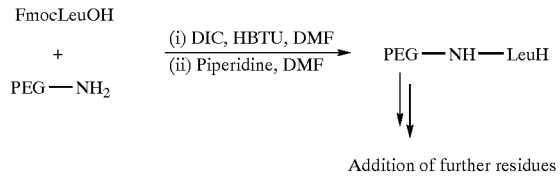

Addition of further residues

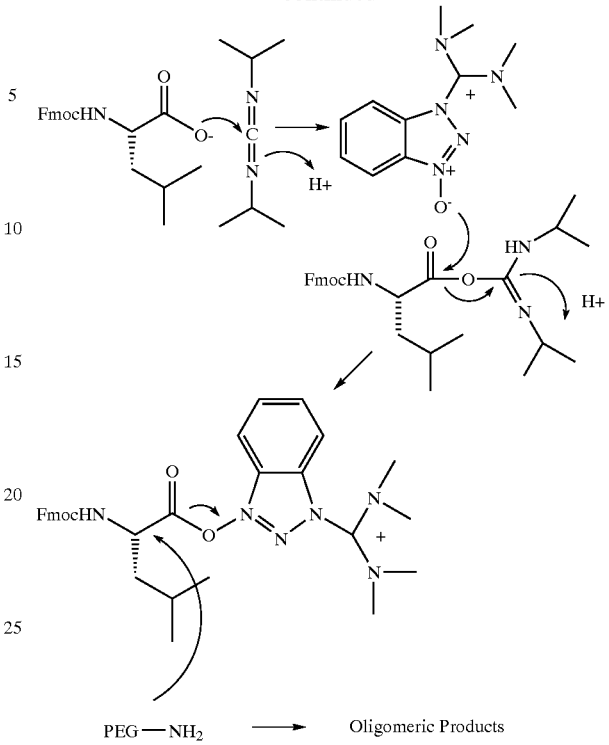

PEG — NH$_2$ ⟶ Oligomeric Products

Synthesis of [H(L-Leu)$_1$NH]$_2$PEG

Coupling: FmocLeuOH (2.884 g, 2 eq) was dissolved in dry DMF (70 ml), and stirred under N$_2$ at RT. DIC (1.278 ml, 2 eq) was added, followed by HBTU (3.095 g, 2 eq) and then amino-PEG (4.500 g, 1 eq). The coupling was monitored by Kaiser testing[10]. After 6 days, the solvent was removed in vacuo and the solid product washed in a Soxhlet extractor with refluxing diethyl ether (ca 10 min/cycle for 3 h) and the soluble product extracted with THF (Ca 30 min/cycle, overnight). NMR of the ether soluble fractions (mainly excess FmocLeuOH) showed no PEG to be present.

Deprotection: The THF soluble product, [Fmoc(L-Leu)l NH]$_2$PEG was dissolved in dry DMF (80 ml) and piperidine (20 ml), and stirred under N$_2$ at RT for 20 h. The solvents were removed in vacuo and the solid product washed in a sinter with diethyl ether (×5) to remove the deprotection by-product, then the soluble product was washed through the sinter with THF, which was subsequently removed in vacuo to leave [H(L-Leu)$_1$NH]$_2$PEG (5.09 g, quantitative yield).

Synthesis of [H(L-Leu)$_2$NH]$_2$PEG

Coupling: [H(L-Leu)$_1$NH]$_2$PEG (4.54 g, 1 eq) was dissolved in dry DMF (60 ml), and stirred under N$_2$ at RT. FmocLeuOH (2.572 g, 2 eq), HBTU (2.760 g, 2 eq) and DIC (1.140 ml, 2 eq) were added. A Kaiser test, after 44 h, took 1 min to go blue; the solvent was then removed in vacuo and the solid product washed several times in a sinter funnel with diethyl ether (3.79 g of ether soluble product was collected). The soluble product (5.25 g, 90% y) was extracted by washing several times with THF. Deprotection: The THF soluble product, [Fmoc(L-Leu)$_2$NH]$_2$PEG was dissolved in dry DMF (80 ml) and piperidine (20 ml), and stirred under N$_2$ at RT for 20 h. The solvents were removed in vacuo and the solid product washed in a sinter with diethyl ether (×5) to remove the deprotection by-product (0.92 g), then the soluble product was washed through the sinter with THF, which was subsequently removed in vacuo to leave [H(L-Leu)$_2$NH]$_2$PEG (4.11 g). An NMR spectrum was obtained (section 13).

Synthesis of [H(L-Leu)$_3$NH]$_2$PEG

Coupling: [H(L-Leu)$_2$NH]$_2$PEG (3.59 g, 1 eq) was dissolved in dry DMF (50 ml), and stirred under N$_2$ at RT. FmocLeuOH (1.908 g, 2 eq), HBTU (2.048 g, 2 eq) and DIC (0.845 ml, 2 eq) were added. A Kaiser test, after 48 h, took 30 s to go blue, however the solvent was still removed in vacuo at this time and the solid product washed several times in a sinter funnel with diethyl ether (1.47 g of ether soluble product was collected). The THF soluble product (4.79 g) was extracted by washing several times with THF, then removing this solvent in vacuo.

Deprotection: The THF soluble product, [Fmoc(L-Leu)$_3$NH]$_2$PEG was dissolved in dry DMF (80 ml) and piperidine (20 ml), and stirred under N$_2$ at RT for 2 days. The solvents were removed in vacuo and the solid product washed in a sinter with diethyl ether (×5), then the soluble portion was washed through the sinter with THF, which was removed in vacuo to leave [H(L-Leu)$_3$NH]$_2$PEG (4.53 g). It was found that although washing the product with toluene extracted much of the yellow discoloration which had accumulated at this stage of the synthesis, PEG was observed in the NMR spectrum of the residue left by removing the toluene.

Synthesis of [H(L-Leu)$_4$NH]$_2$PEG

Coupling: [H(L-Leu)$_3$NH]$_2$PEG (3.24 g, 1 eq) was dissolved in dry DMF (50 ml), and stirred under N$_2$ at RT. FmocLeuOH (1.59 g, 2 eq), HBTU (1.705 g, 2 eq) and DIC (0.704 ml, 2 eq) were added. After 48 h the solvent was removed in vacuo and the solid product washed several times in a sinter funnel with diethyl ether. The soluble product (4.26 g) was extracted by washing several times with THF, then removing this solvent in vacuo.

Deprotection: The THF soluble product, [Fmoc(L-Leu)$_4$NH]$_2$PEG was dissolved in dry DMF (60 ml) and piperidine (15 ml), and stirred under N$_2$ at RT for 2 days. The solvents were removed in vacuo and the solid product washed in a sinter with diethyl ether (×5), then the soluble product was washed through the sinter with THF, which was removed in vacuo to leave the product [H(L-Leu)$_4$NH]$_2$PEG (3.39 g). It was found that although stirring the product with decolourising charcoal extracted only some of the yellow coloration (2.25 g of product was recovered after this purification attempt).

Testing of the Exact Chain Length Polyleucines in the UHP Conditions

Catalyst (50 mg of 1 mer, 2 mer, 3 mer or 4 mer) and chalcone (25 mg, 0.120 mmol) is placed in a vial. UHP (1.5 g) is stirred under N$_2$ in THF for 40 min, filtered and titrated: 20 ml of this solution is found to decolourise 116.8 mg of acidified aqueous KMnO$_4$. 1.8 ml of this solution (1.38 eq of H$_2$O$_2$) is then added to each vial, together with DBU (27 uL, 1.5 eq) to begin the reactions. After 17 h, UHP (100 mg) and DBU (100 ml) are added directly into each reaction.

| Time | 1mer % C/% ee | 2mer % C/% ee | 3mer % C/% ee | 4mer % C/% ee |
|---|---|---|---|---|
| 1 h | 3/1 | — | 19/11 | 7/9 |
| 15 h | 20/3 | 19/4 | 23/6 | 13/7 |
| 40 h | 98/1 | 96/2 | 85/3 | 98/1 |

Example 8

Further Test Results with the 5, 10, 16. 20 and 25 mers

Using THF/TBME/H$_2$O$_2$ Conditions:

Soluble catalyst (Xmg such that 1×10$^{-5}$ moles of chains of polyleucine were present) and chalcone (50 mg) were placed in vials and pre-stirred in THF (1 ml) and DBU (56 uL, 1.5 eq) for 25 min. H$_2$O$_2$ in TBME (0.5 ml, 1.69 eq) was then added to start the reaction.

To make this solution, 12 ml of 30% aq H$_2$O$_2$ was dried for 30 min with MgSO$_4$ (20.0 g) in TBME (50 ml), then filtered to another conical flask containing MgSO$_4$ (20.0 g), more TBME (20 ml) was used for the filtration. This suspension was stirred for 50 min. After filtration, 0.5 ml of this solution decolourised 25.7 mg of acidified aqueous KMnO$_4$. The concentration of H$_2$O$_2$ in this solution was shown to be stable with time, but the solution may not have been properly dry (high rate of background reaction).

Molecular sieves dry H$_2$O$_2$ solutions in TBME. A 92% ee was obtained for the epoxidation of chalcone with a solid polyleucine catalyst, but the concentration of H$_2$O$_2$ decreases rapidly (e.g. from 0.8M to 0.2M in 10 min) so this method couldn't be used for adding a solution of oxidant to various reactions sequentially. HPLC results are tabulated below:

| PLL used | Xmg | % C (2 h) | % ee (2 h) | % C (4 h) | % ee (4 h) | % C (20 h) | % ee (20 h) |
|---|---|---|---|---|---|---|---|
| B'GR'ND | 0 | 41 | 1 | 56 | 1 | 63 | 0 |
| 1st 3mer | 13.0 | 43 | 3 | 61 | 2 | 94 | 2 |
| 2nd 3mer* | 13.0 | 35 | 4 | 44 | 3 | 70 | 5 |
| 5mer# | 15.6 | 53 | 23 | 72 | 18 | 100 | 18 |
| 10mer | 19.5 | 53 | 23 | 70 | 19 | 98 | 14 |
| 15mer | 24.8 | 62 | 29 | 63 | 35 | 96 | 29 |
| 20mer | 24.1 | 51 | 15 | 68 | 12 | 96 | 10 |
| 25mer† | 28.2 | 52 | 29 | 59 | 26 | 65 | 27 |
| CLAMPS | 43.7 | 72 | 43 | 98 | 31 | 100 | 37 |

*No microanalysis data on 2nd 3mer, so PLL content was assumed to be the same as the first.
†Used earlier to test out these conditions, with a higher ee (52% at 49% C and 44% at 90% C). It seems likely that this solution was drier than that used for the simultaneous tests carried out above.
Anhydrous TBHP (a solution in decane) gave a very low ee with the soluble 5mer, though the reaction did proceed.

Example 9

Adsorbtion of a Soluble Catalyst onto Silica[11]

The 10 mer soluble polyleucine (213 mg) and silica (725 mg) were stirred slowly in THF (6 ml) at RT for 48 h. The resulting silica adsorbed catalyst was filtered into a sinter funnel, where it was washed with THF (3×10 ml), EtOH (3×10 ml) and THF again (2×10 ml). From the sinter 692 mg of silica-bound 10 mer was collected, from the filtrate 147 mg of the 10 mer was recovered. Along with the 5 mer of soluble polyleucine grown in methanol, these 2 catalysts were tested in the homogeneous UHP/THF conditions used for testing the 5 mer- 25 mer series.

5 mer (MeOH) grown (silica free)

To Catalyst (11.7 mg) and chalcone (11.7 mg) was added solution X (1.17 ml). After 2 h and 23 h was added solution Y (0.29 ml). 10 mer (on silica, or free from it)

To catalyst (45.7 mg) and chalcone (45.7 mg) was added solution X (4.57 mL). After 2 h and 23 h was added solution Y (1.14 ml).

Solution X: UHP (0.5 g) was stirred under N$_2$ at RT for 20 min in THF (49.5 ml) and DBU (0.5 ml) and filtered.

Solution Y: UHP (2.02 g) was stirred under $N_2$ at RT for 20 min in THF (50 ml) and filtered.

| Time | 5mer grown in MeOH % C/% ee | 10mer on silica % C/% ee | free 10mer from filtrate % C/% ee |
|---|---|---|---|
| 1 h | 1/63 | 13/91 | 39/98 |
| 2 h | 2/61 | 27/81 | 41/98 |
| 6 h | 6/58 | 42/90 | 87/97 |
| 23 h | 7/58 | 66/87 | 98/97 |
| 48 h | 12/47 | 78/84 | 100/97 |

Example 10

Preparation & Polymerisation of Leucine-NCA

Preparation of Leucine-NCA

Leucine (15 g, 11.44 mmol) was dried under high vacuum overnight at 90° C. and after cooling to 50° C. was suspended in THF (180 ml). Triphosgene (13.51 g, 0.4 eq) previously dissolved in THF (50 ml) was slowly added over 30 minutes. The mixture was stirred for 1 h after which a clear solution was obtained. After stirring for a further 1 h, the solvent was removed in vacuo and the residue dissolved in a minimum amount of toluene (ca 100 ml). Precipitation of the product was initiated by the addition of n-hexane (ca 200 ml). The product was filtered, washed twice with n-hexane (2×100 ml) and dried to obtain 12.17 g (85%) of L-leucine-NCA as a white crystalline solid.

Polymerisation of the leucine-NCA

The reaction was set up with the intended product being $H(L-Leu)_x NHPEG-Y$ where Y=MeO and X=15. MeO-PEG-$NH_2$ was used as initiator.

15 mer initiator 5.00 g; L-Leu-NCA 2.40 g (15 eq); THF 200 ml

The reaction was monitored by IR. After 5 days, only a small amount of L-Leu-NCA was observed and after 7 days, all the L-Leu-NCA was completely consumed.

Workup: After 7 days, the reaction mixture was concentrated to about ⅓ its original volume and the solid precipitated by adding diethyl ether (300 ml). The suspension was stirred in an ice bath for 30 minutes and the resulting solid filtered, washed with ether (2×150 ml) and dried under vacuum for 2 h to yield 6.5 g of crude material. This was dissolved in THF (250 ml) and filtered through paper to removed insoluble residues. The filtrate was concentrated in vacuo and the product precipitated by adding ether (200 ml). This was filtered, washed with ether (2×100 ml) and dried under vacuum for 6 h to give 4.5 g (ca 66%) of $H(L-Leu)_x NHPEG-Y$.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, or related fields are intended to be within the scope of the following claims.

References

1 For reviews see (a) Ebrahim, S.; Wills, M. *Tet rahedron Asymm.* 1997, 8, 3163; (b) Pu, L. *Tetrahedron Asymm.* 1998, 9, 1457; (c) Porter, M. J.; Roberts, S. M.; Skidmore, J. *Bioorg. Med. Chem.* 1999, 7, 2145.

2. Julia, S., Masana, J., Vega, J.; *Angew. Chem., Int. Ed. Engl.*, 1980, 19, 929.

3. Bentley, P. A.; Bergeron, S.; Cappi, M. W.; Hibbs, D. E.; Hursthouse, M. B.; Nugent, T. C.; Pulido, R.; Roberts, S. M.; Wu, L. E. *J. Chem. Soc. Chem. Commun.*, 1997, 739.

4. Allen, J. V.; Drauz, K-H.; Flood, R. W.; Skidmore, J. *Tet Lett.* 1997,40, 5417.

5. Adger, B. M.; Barkley, J. V.; Bergeron, S.; Cappi, M. W.; Flowerdew, B. E.; Jackson, M. P.; McCague, R.; Nugent, T. C.; Roberts, S. M. *J. Chem. Soc, Perkin Trans.* 1, 1997, 3501.

6. Cappi, M. W.; Chen, W-P., Flood.; Liao, Y-W., Roberts, S. M.; Skidmore, J., Smith, J. A.; Williamson, N. M. *J. Chem. Soc. Chem. Commun.*, 1998, 1159.

7. Gravert, D. J.; Janda, K. D.; *Chem. Rev.*, 1997, 97, 489.

8. Bentley, P. A.; Cappi, M. W.; Flood, R. W.; Roberts, S. M., Smith, J. A.; *Tetrahedron Lett*, 1998, 39, 9297.

9. Volk, M.; Petty, S. A; Org. Lett 2001.

10. NovaBiochem Catalogue, 1999, pS43 (For Kaiser test); E. Kaiser, et.al., *Anal. Biochem.*, 1970, 34, 595.

11. Geller, T. G.; Final Report, p7.

What is claimed is:

1. A process for the addition of a nucleophile across an electron poor carbon-carbon double bond (a Michael addition) comprising contacting in a solvent
   (i) a nucleophile;
   (ii) a compound comprising an electron poor carbon-carbon double bond; and
   (iii) a catalyst comprising a soluble polymer (SSL) and a polyamino acid (PAA) wherein said catalyst is soluble in the solvent.

2. A process according to claim 1 wherein the nucleophile is selected from oxygen and sulphur.

3. A process according to claim 2 wherein the nucleophile is oxygen.

4. A process according to claim 3 wherein the oxygen nucleophile is provided by a peroxide group.

5. A process according to claim 2 wherein the sulphur nucleophile is provided by a ⁻SPh group.

6. A process according to claim 1 wherein the electron withdrawing group is selected from carbonyl, —CN and —$NO_2$.

7. A process according to claim 6 wherein the electron withdrawing group and the carbon-carbon double bond comprise an enone group.

8. A process according to claim 1 wherein the compound comprising the electron poor double bond is

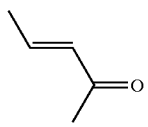

9. A process according to claim 1 wherein the catalyst is of the formula or comprises a group of the formula
   SSL-linker-PAA,
   wherein linker is a linker bond or an optional linker group.

10. A process according to claim 9 wherein the catalyst is of the formula X-SSL-linker-PAA-Y,
    wherein X and Y are independently selected from OMe and $NH_2$.

11. A process according to claim 9 wherein the catalyst is of the formula X-PAA-linker-SSL-linker-PAA-Y,
    wherein X and Y are independently selected from OMe and $NH_2$.

12. A process according to claim 10 wherein Y is $NH_2$.

13. A process according to claim 9 wherein the linker bond is an amide bond.

14. A process according to claim 1 wherein the polyamino acid is a homopolymer of one, or a copolymer consisting of two or more, amino acids selected from cysteine, glycine, neopentylglycine, alanine, valine, leucine, norleucine, phenylalanine, tyrosine, serine, cystine, threonine, methionine, di-iodotyrosine, thyroxine, dibromotyrosine, tryptophan, proline, hydroxyproline, aspartic acid, glutamic acid, β-hydroxyglutamic acid, ornithine, arginine, lysine and histidine.

15. A process according to claim 14 wherein the polyamino acid is a homopolymer of one, or a copolymer consisting of two or more, amino acids selected from leucine, alanine and neopentylglycine.

16. A process according to claim 1 wherein the soluble polymer is a homopolymer or a copolymer of monomers selected from styrene, vinyl alcohol, ethylene imine, acrylic acid, methylene oxide, ethylene glycol, propylene oxide and acrylamide.

17. A process according to claim 1 wherein the soluble polymer is polyethylene glycol (PEG).

* * * * *